United States Patent
Jung

(10) Patent No.: US 6,605,268 B2
(45) Date of Patent: Aug. 12, 2003

(54) TOOTH PASTE COMPOSITION CONTAINING ROSE-SEED OIL

(76) Inventor: Myung Woo Jung, 943-1, Sihung 3-dong, Gumchun-ku, Seoul (KR), 153-033

(*) Notice: Subject to any disclaimer, the term of this patent is extended or adjusted under 35 U.S.C. 154(b) by 0 days.

(21) Appl. No.: 09/949,708

(22) Filed: Sep. 12, 2001

(65) Prior Publication Data

US 2002/0022006 A1 Feb. 21, 2002

Related U.S. Application Data

(63) Continuation of application No. PCT/KR99/00357, filed on Jul. 5, 1999.

(30) Foreign Application Priority Data

Mar. 12, 1999 (KR) ......................... 99-0008435

(51) Int. Cl.$^7$ ............................. A61K 7/16; A61K 7/26
(52) U.S. Cl. .......................... 424/58; 424/49; 514/900; 514/902
(58) Field of Search ....................... 424/49–88; 514/900, 514/902

(56) References Cited

U.S. PATENT DOCUMENTS

| | | | | |
|---|---|---|---|---|
| 2,470,906 A | * | 5/1949 | Taylor .......................... | 167/93 |
| 3,992,519 A | * | 11/1976 | Hofmann et al. .............. | 424/48 |
| 4,724,136 A | * | 2/1988 | Scheibl ......................... | 424/50 |
| 4,963,346 A | * | 10/1990 | Amer ........................... | 424/49 |
| 4,985,235 A | * | 1/1991 | Kligman ...................... | 424/49 |
| 5,032,384 A | * | 7/1991 | Yeh et al. ..................... | 424/49 |
| 5,149,521 A | * | 9/1992 | Hirose et al. ................. | 424/58 |
| 5,188,817 A | * | 2/1993 | Ozick ........................... | 424/49 |
| 5,470,565 A | * | 11/1995 | Hayakawa et al. ........... | 424/52 |
| 5,646,178 A | * | 7/1997 | Walker et al. ................ | 514/456 |
| 5,650,432 A | * | 7/1997 | Walker et al. ................ | 514/456 |
| 5,683,678 A | * | 11/1997 | Heckert et al. ............... | 424/52 |
| 5,925,335 A | * | 7/1999 | Shuch et al. .................. | 424/49 |

FOREIGN PATENT DOCUMENTS

| | | | |
|---|---|---|---|
| EP | 301975 | * 2/1989 | |
| EP | 91114582.9 | 8/1991 | ............ A61K/7/16 |
| EP | 94100522.5 | 1/1994 | ............ A61K/7/46 |
| EP | 1046398 | * 10/2000 | |
| EP | 1072254 | * 1/2001 | |
| FR | 2461499 | * 2/1981 | |
| WO | 99/55298 | * 4/1999 | |
| WO | 99/44574 | * 9/1999 | |

OTHER PUBLICATIONS

Merck Index (12$^{th}$ ed) entry 8333 Retinoic acid (Vitamin A Acid/Tretinoin) entries 9632 9633 9634 9635 9636 9637 9638 Tocopioerols (Vitamin E) entry 867 Ascorbic Acid (Vitamin C), 1996.*
English Language Abstract Caplus 114: 253903 1991 of Pareta et al An. R. Acad. Farm. 56(2): 283–293 (1990) Identification of the Active Principles of Oil of Rosa Rubioinose Seed Oil (Tretinoin/Trans–Retinoic Acid), 1990 (1991).*
Rosa Rubiginosa—Database Search Results, www.scs.leeds.ac.uk, Rosa Rubiginosa—Essential Botanicals.com, Feb. 5, 2002.*
Steinmetz CODEX Vegetabalis entry 976 Rosa Canina (Seed) Hocking A Dictionary of Terms in Pharmacognosy p 193–194 Rosa Rose Arctander Perfume and Flavor Materials of Natural Origin Rose Entries cols. 551–557, 1953, 1955, 1960.*
Abstract of "Rosa Rubiginosa" Rose Hip Seed Oil Constituents Web Site Info Downloaded Kuseva Rastenievud Nauki (1974) 11(2): 53–58 is very similar to Caplus 81: 111396 Essential oil in Rose Seeds or from Rose Petals, 1974.*

* cited by examiner

*Primary Examiner*—Shep K. Rose
(74) *Attorney, Agent, or Firm*—Jacobson Holman PLLC

(57) ABSTRACT

Provided with a tooth paste composition which contains an abrasive cleaning agent, a humectant, a binder or thickener and a flavouring agent, the tooth paste, and includes a rose-seed oil, wherein the rose-seed oil is contained in an amount of 1–6% by weight based on the total weight of the tooth paste composition.

4 Claims, No Drawings

TOOTH PASTE COMPOSITION CONTAINING ROSE-SEED OIL

This is a Continuation Application of PCT International Application No. PCT/KR99/00357, filed Jul. 5, 1999.

BACKGROUND OF THE INVENTION

1. Field of the Invention

The present invention relates to a tooth paste composition efficacious for a preventive and remedy against a paradental disease and a preventive against caries and, more particularly, to a composition for dental hygiene in which use is made of a rose-seed oil to prevent and treat a paradental disease or prevent caries.

2. Description of the Related Art

Brushing the teeth with a toothbrush and a tooth paste is the most general measure to maintain dental hygiene. The reason why the tooth paste is used lies in that the tooth paste contains an abrasive and a cleaner which help mechanical removal of plaque, smooth the surface of teeth, rinse the mouth with a refreshed feeling, making it pleasant to clean the mouth. However, this simple method for removing the plaque is not so effective to maintain dental hygiene and prevent paradental diseases, as a result of which more people suffer from paradental diseases with an increase of their age.

It is well known that sodium chloride, anti-plasmin agent, allantoin derivatives, vitamins and amino acids are widely used in a composition for dental hygiene in a sole form or in combination thereof for the purpose of a preventive and cure against paradental diseases and a preventive against a caries. However, these substances are not effective and there is a demand for a new tooth paste composition that takes an effect against the paradental diseases in three ways: eliminating causal bacteria, reducing inflammation of the teethridge, etc., and restoring a tissue such as teethridge.

SUMMARY OF THE INVENTION

Accordingly, an object of the present invention is to provide a tooth paste composition efficacious against paradentitis, gingivitis, caries, stomatitis, etc.

That is, the object of the present invention is to provide a tooth paste composition containing a rose-seed oil efficacious against paradental diseases, in which the rose-seed oil which has been reported to be effective in regeneration of skin, reduction and restoration of wound and treatment of inflammation is added to a tooth paste base.

To achieve the object of the present invention, there is provided a tooth paste composition which contains an abrasive cleaning agent, a humectant, a binder and a flavouring agent; the tooth paste comprises a rose-seed oil. More preferably, the rose-seed oil is contained in an amount of 1–6% by weight based on the total weight of the tooth paste composition.

The toothpaste composition is most preferably to be stored in a light-impeding container. The toothpaste composition therapeutic potency at room temperature in a light impeding or other type of container.

DETAILED DESCRIPTION OF PREFERRED EMBODIMENT

Now, the present invention will be described in detail.

It is reported that a rose-seed oil is effective for nourishment and regeneration of the skin (See. British Journal of Dermatology, April 1997), reduction and treatment of the wound and treatment of the burned skin (See. Cancer Chemotherapy and Pharmacology, March 1979), inflammation of the skin (See. American Journal of Obstetrics and Gynecology) and pimple (See. Journal of American Academy of Dermatology).

According to a toxicological experiment in which the rose-seed oil is administered to a rat, it is demonstrated that the rose-seed oil has no harm to the human body with LD 50, that is, 5 g/kg (weight). The rose-seed oil is also turned out to be nonpoisonous to the skin, in another experiment.

The rose-seed oil used herein is derived from a rose whose botanical name is Rosa aff. Rubignosa L that is grown naturally or artificially in a wet climate. The rose has thorny stem and branches and the flowers are white and pink, or in some times, yellow. The flower is 3–6 cm in size and has 5 flower cups per 7–15 buds. The floral stalk is 2 mts long and about 3 mts in radius, and the leaves are oval and green-colored. The rose has about 15–20 fruits containing an ordinary oil. The fruits are reddish and egg-shaped with a diameter of 1.5–2.5 mm. The outer skin of the fruit is 1–3 mm thick and contains a large content of ascorbic acid and pectin and a small content of sugar. The seeds consist of unsaturated fatty acid, tretinoin, gums, margarine, cartenoides, cetonic, etc. Gums, margarine and cartenoides are removed in the course of extraction of the oil.

The extraction of the rose-seed oil includes the two steps of dissolving the rose seeds in a solvent, and distilling the oil-containing extracted solvent i.e., micella to recover the solvent and then separating the oil. The solvent used herein is petroleum benzene, benzol, hexane, or the like. To extract the rose-seed oil, the rose seeds carefully selected are pressed into flakes in order for the solvent to be penetrated into the seeds. The flakes are strengthened under conditions of 3–11% water content and a temperature of 50–60 degrees. These flakes are then added to an extractor to extract the solvent. The solvent is separated from the micella obtained through the extraction in two steps of volatilization and stripping. The micella generated from the extractor contains a 25–30% oil content. The oil content is increased to 90–95% by volatilizing the solvent. The concentrated micella is transferred to an apparatus called a stripper in which the micella is brought in direct contact with water vapors in a vacuum of about 50–200 mmHg to perfectly remove the residual solvent and obtain the rose-seed oil.

It is preferable that the present tooth paste composition contains 1–6% by weight of the rose-seed oil based on the total weight of the composition. The other components may be a mixture of the gradients of an ordinary tooth paste composition.

For example, a humectant used herein is at least one or two substances selected from the group consisting of glycerine, sorbitol solution and amorphous sorbitol solution. An abrasive cleaning agent used herein is calcium hydrogen phosphate, calcium carbonate, aluminum oxide, etc. Additives used in a small content are ordinary components used in the tooth paste and include sweetening agents, pH controlling agents, antiseptic substances, coloring agents and binders.

The sweetening agents are sodium saccharide, aspartame, etc., the pH controlling agents are sodium phosphate, disodium phosphate, citric acid, etc., and the antiseptic substances are paraoxy benzoin methyl, sodium benzoin, etc.

The binders or thickeners are sodium carboxymethyl cellulose, carrageenan, xantan gum, etc. A foaming agent used herein may be anionic and non-ionic surfactants of sodium lauryl sulfate, saccharose carboxylic ester and sorbitan carboxylic ester in a sole form or in a combination of at least two thereof.

An flavouring agent used herein is a mixture of peppermint oil, spearmint oil, menthol, etc., and other additives are enzymes such as dextranase, etc.

The preparation of the tooth paste composition in the present invention comprises: dispersing a small powder content of sodium carboxymethyl cellulose, saccharine and the like in a humectant e.g., amorphous sorbitol solution, diluting the solution with a purified water, first mixing the solution and the purified water in a mixer, adding an abrasive cleaning agent such as calcium hydrogen phosphate, etc. and then 1–6% by weight of a rose-seed oil, and adding a foaming agent, a stabilizer, an flavouring agent, etc.

Reference will be made to embodiments and comparative examples for the detail description of the present invention.

EMBODIMENTS 1–5 AND COMPARATIVE EXAMPLE 1

A tooth paste is prepared with the components listed in Table 1 in order to implement experimental examples of the present invention.

TABLE 1

| Components | C1 | E1 | E2 | E3 | E4 | E5 |
| --- | --- | --- | --- | --- | --- | --- |
| Calcium Hydrogen Phosphate | 40% | 40% | 40% | 40% | 40% | 40% |
| Amorphous Sorbitol | 25% | 25% | 25% | 25% | 25% | 25% |
| Rose-Seed Oil | 0% | 1% | 3% | 5% | 6% | 10% |
| Sodium Alkyl Sulfate | 2% | 2% | 2% | 2% | 2% | 2% |
| Sodium Saccharide | 0.1% | 0.1% | 0.1% | 0.1% | 0.1% | 0.1% |
| Carboxyl Methyl Cellulose | 1% | 1% | 1% | 1% | 1% | 1% |
| Peppermint Oil | 0.8% | 0.8% | 0.8% | 0.8% | 0.8% | 0.8% |
| Plus Purified Water | 100% | 100% | 100% | 100% | 100% | 100% |

Note:
C1: Comparative Example 1; and
E1–E5: Embodiments 1–5.

EXPERIMENTAL EXAMPLE 1

Preventive Efficacy of Tooth Pastes (Embodiments 1–5 and Comparative Example 1) Against Paradental Diseases 1) Efficacy Against Gingivitis For the experiment, 50 persons who suffer from gingivitis rinse the mouth with the tooth pastes of the present invention and Comparative Example 1 two or three times a day for 30 days. The tooth paste of Comparative Example 1 takes no effect on the patients. The tooth pastes of Embodiments 1–4 are efficacious for 42 persons out of 50. The tooth paste of Embodiment 5 is also effective, but causes an unpleasant feeling with a bad smell of oil and less foams with an increase in the oil content.

2) Efficacy Against Paradentitis

For the experiment, 30 persons who suffer from paradentitis rinse the mouth with the tooth pastes of the present invention and Comparative Example 1 two or three times a day for 30 days. The tooth pastes of Embodiments 2–4 are efficacious for 23 persons out of 30, but those of Comparative Example 1 and Embodiment 5 have the same effect as for the gingivitis.

3) Efficacy Against Caries and Stomatitis

For the experiment, 36 persons who suffer from caries and stomatitis rinse the mouse with the tooth paste of the present invention and Comparative Example 1 two or three times a day for 20 days. As a result, the tooth pastes take an effect on 30 persons.

4) The tooth pastes provide an abrasion resistance of teeth and are effective against inflammation in the mouth.

As described above, the tooth paste composition containing a rose-seed oil according to the present invention takes an effect against gingivitis, paradentitis, caries and stomatitis and has an abrasion resistance for he teeth.

It will be apparent to those skilled in the art that various modifications and variations can be made in the present invention without departing from the spirit or scope of the invention. Thus, it is intended that the present invention covers the modifications and variations of this invention provided they come within the scope of the appended claims and their equivalents.

What is claimed is:

1. A method of treating or preventing an amenable paradental disease, enhancing abrasion resistance of teeth and/or combating inflammation of gums which comprises brushing one's teeth with a tooth paste composition comprising 1–6% of rose-seed oil extracted from seeds of Rosa Aff. Rubiginosa L.

2. The method of claim 1 for treating or preventing a paradental disease.

3. The method of claim 1 for enhancing abrasion resistance to teeth.

4. The method of claim 1 for combating gum inflammation.

* * * * *